United States Patent
Kikuchi et al.

(10) Patent No.: US 7,037,312 B2
(45) Date of Patent: May 2, 2006

(54) INSERTION DEVICE FOR DEFORMABLE INTRAOCULAR LENS

(75) Inventors: Toshikazu Kikuchi, Hachioji (JP);
Kenichi Kobayashi, Tokyo (JP);
Hidenori Yoshida, Funabashi (JP); Koji Shimura, Yokohama (JP)

(73) Assignee: Canon-Staar Co., Inc., (JP)

( * ) Notice: Subject to any disclaimer, the term of this patent is extended or adjusted under 35 U.S.C. 154(b) by 602 days.

(21) Appl. No.: 10/222,419

(22) Filed: Aug. 16, 2002

(65) Prior Publication Data

US 2003/0050646 A1  Mar. 13, 2003

(30) Foreign Application Priority Data

Sep. 7, 2001 (JP) ............................ 2001-272433
May 8, 2002 (JP) ............................ 2002-133181

(51) Int. Cl.
*A61B 17/00* (2006.01)
(52) U.S. Cl. .................................................. 606/107
(58) Field of Classification Search ............... 606/107, 606/108, 138, 166; 604/15; 623/4.11, 6.11
See application file for complete search history.

(56) References Cited

U.S. PATENT DOCUMENTS

| | | | |
|---|---|---|---|
| 5,496,328 A | | 3/1996 | Nakajima et al. |
| 5,522,890 A | * | 6/1996 | Nakajima et al. .......... 623/6.46 |
| 5,620,450 A | * | 4/1997 | Eagles et al. ............... 606/107 |
| 5,772,666 A | * | 6/1998 | Feingold et al. ............ 606/107 |
| 5,873,879 A | * | 2/1999 | Figueroa et al. ............ 606/107 |
| 5,947,975 A | * | 9/1999 | Kikuchi et al. ............. 606/107 |
| 6,666,871 B1 | * | 12/2003 | Kikuchi et al. ............. 606/107 |

FOREIGN PATENT DOCUMENTS

| | | |
|---|---|---|
| JP | 58-146346 | 8/1983 |
| JP | 4-212350 | 8/1992 |
| JP | 5-103803 | 4/1993 |
| JP | 5-103808 | 4/1993 |
| JP | 5-103809 | 4/1993 |
| JP | 7-23990 | 1/1995 |
| JP | 7-23991 | 1/1995 |
| JP | 7-212350 | 8/1995 |
| JP | 8-38542 | 2/1996 |
| JP | 9-506285 | 6/1997 |
| JP | 11-510711 | 9/1999 |
| JP | 2000-60880 | 2/2000 |
| JP | 2001104347 | 4/2001 |

* cited by examiner

*Primary Examiner*—Julian W. Woo
*Assistant Examiner*—Victor X. Nguyen
(74) *Attorney, Agent, or Firm*—Roth & Goldman, P.A.

(57) ABSTRACT

An intraocular-lens insertion device is adapted to deform a deformable intraocular lens into a smaller size and insert the intraocular lens into an eye via an insertion tube. An intraocular-lens guide is provided on the inner surface of the insertion tube. The guide may be a rail-shaped projection or a groove, which extends parallel to a direction along which the intraocular lens is pushed out. A stress release structure is provided on the insertion tube in order to release stress of the intraocular lens produced due to deformation thereof. Moreover, a frictional-resistance increasing structure is provided on the inner surface of the insertion tube to be located in the vicinity of the stress release structure. The frictional-resistance increasing structure increases frictional resistance between the inner surface of the insertion tube and the intraocular lens. The frictional-resistance increasing structure may be a roughened surface which completely or partially covers the inner surface of the insertion tube.

5 Claims, 10 Drawing Sheets

FIG. 22

INSERTION DEVICE FOR DEFORMABLE INTRAOCULAR LENS

BACKGROUND OF THE INVENTION

1. Field of the Invention

The present invention relates to an insertion device for inserting a deformable intraocular lens into the eye. Examples of such a deformable intraocular lens include a deformable intraocular lens that is inserted into the eye in place of the natural lens when the latter is physically extracted because of cataracts, and a vision correction lens that is inserted into the eye for the sole purpose of vision correction.

2. Description of the Related Art

Implantation of an intraocular lens for treating cataract has been widely performed since 1949, when Ridley implanted for the first time an artificial lens; i.e., an intraocular lens, into the human eye in place of an opaqued natural lens during cataract surgery.

As disclosed in Japanese Patent Application Laid-Open (kokai) No. 58-146346, there have been invented improved intraocular lenses which can be inserted into the eye through a small incision formed in the eyeball. In one of the improved intraocular lenses, at least an optical portion is made of a deformable elastic material having a predetermined memory characteristic. In another improved intraocular lens, at least an optical portion is made of an elastic material having a predetermined memory characteristic, and there are provided supports which are made of a material different from that of the optical portion and are adapted to support the optical portion within the eye.

Moreover, as disclosed in, for example, Japanese Patent Application Laid-Open (kokai) No. 4-212350, the assignee of the present invention has proposed improved insertion devices. By use of these devices, the optical portion of an intraocular lens is compressed, rolled, bent, stretched, or folded so as to reduce its exterior size, thereby enabling the intraocular lens to be inserted into the eye through a small incision formed in the eyeball. These insertion devices facilitate an operation for implanting an intraocular lens into the eye.

Figure 16:
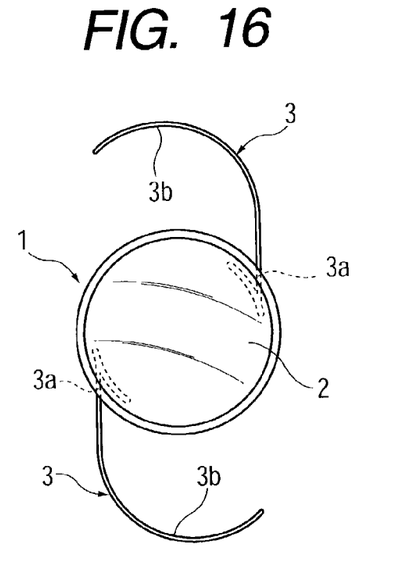
FIG. 16 is a plane view of a conventional deformable intraocular lens.
Figure 17A:
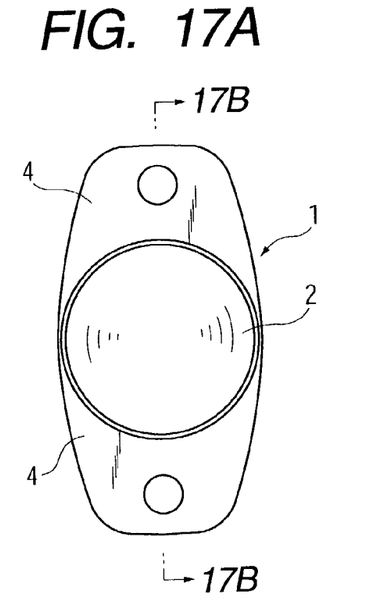
FIG. 17A is a plane view of another conventional deformable intraocular lens.
Figure 17B:
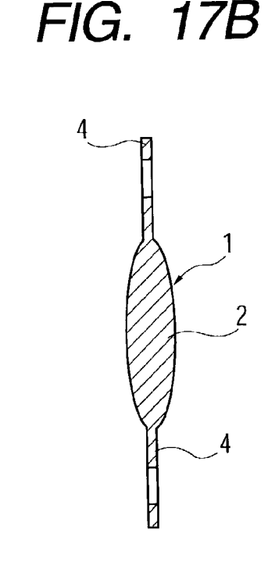
FIG. 17B is a cross sectional view taken along 17B—17B of FIG. 17A.

FIG. 16 and FIGS. 17A and 17B show the conventional deformable intraocular lenses. The deformable intraocular lens 1 shown in FIG. 16 is composed of a circular optical portion 2 and two symmetrically disposed supports 3. The circular optical portion 2 is made of an elastic material having predetermined memory characteristics. The supports 3 are made of a material different from that of the optical portion 2, and bases 3a of the supports 3 are embedded in the peripheral region of the optical portion 2 for fixing, while wire-shaped tails 3b of the supports are curved. The deformable intraocular lens 1 shown FIGS. 17A and 17B is composed of a circular optical portion 2 and a pair of thin plate-shaped support portions 4 that are integral with the optical portion 2. The optical portion 2, like the optical portion 2 shown in FIG. 16, is made of an elastic material having predetermined memory characteristics. The support portions 4 are projected from the periphery of the optical port 2 in opposite directions.

Figure 18:
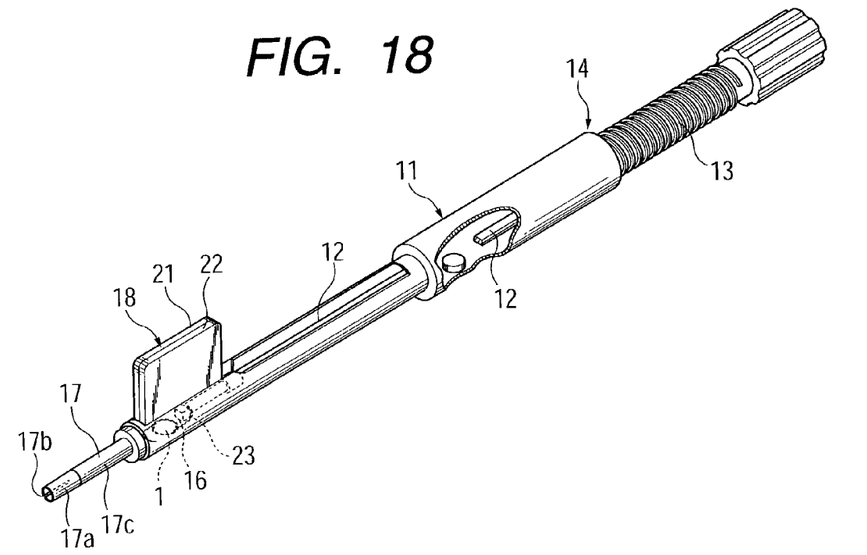
FIG. 18 is a partially cutaway perspective view of a conventional intraocular-lens insertion device.

FIG. 18 is a partially cutaway perspective view of a conventional insertion device for folding and deforming the above-described intraocular lens into a smaller size and for inserting the lens into the eye via an insertion tube.

Figure 19:
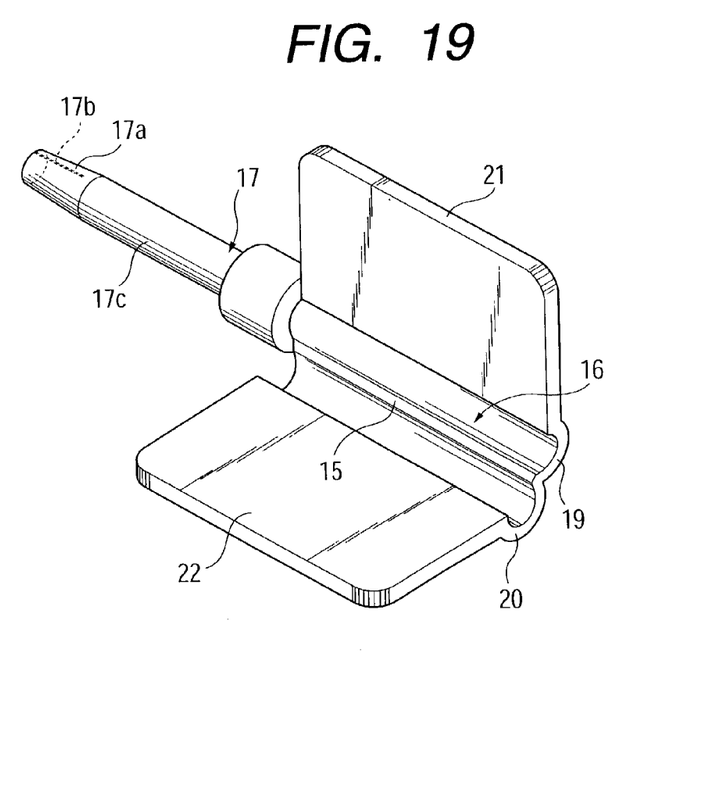
FIG. 19 is an enlarged perspective view of the enclosing member of FIG. 18.
Figure 20:
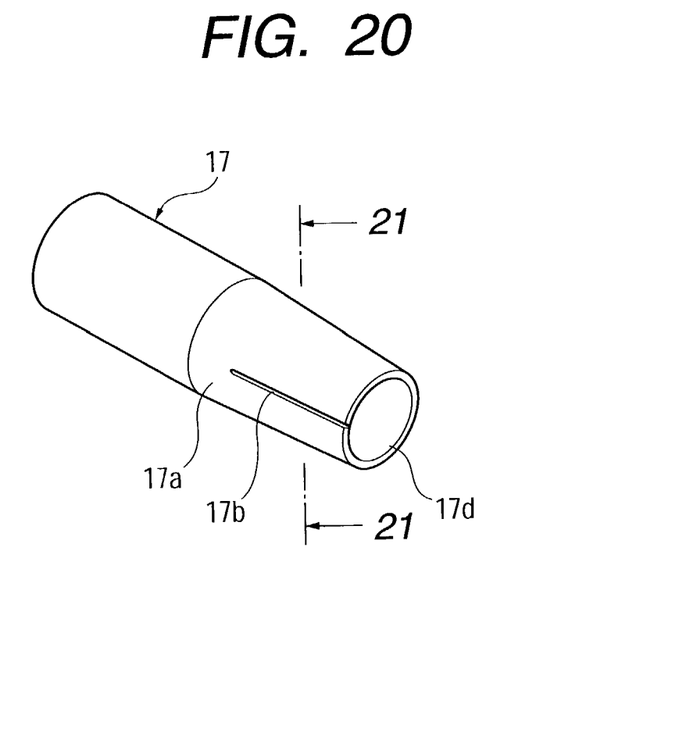
FIG. 20 is an enlarged perspective view of the insertion end portion of FIG. 19.
Figure 21:
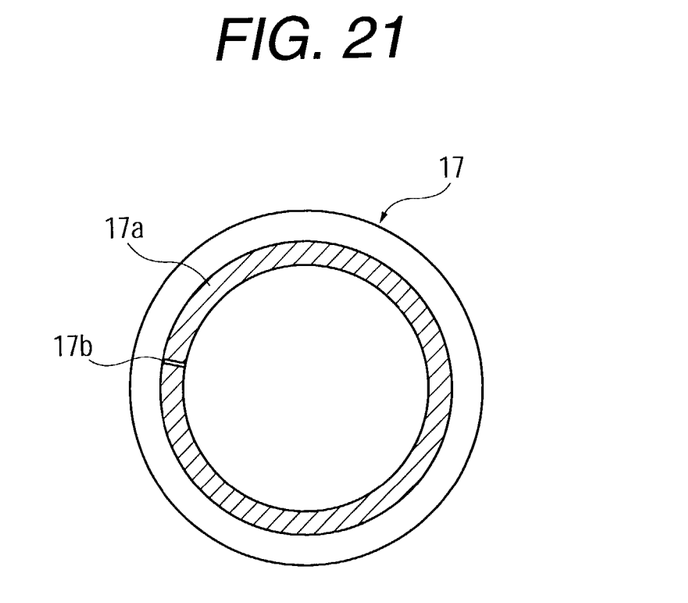
FIG. 21 is a cross sectional view taken along line 21—21 of FIG. 20.
Figure 22:
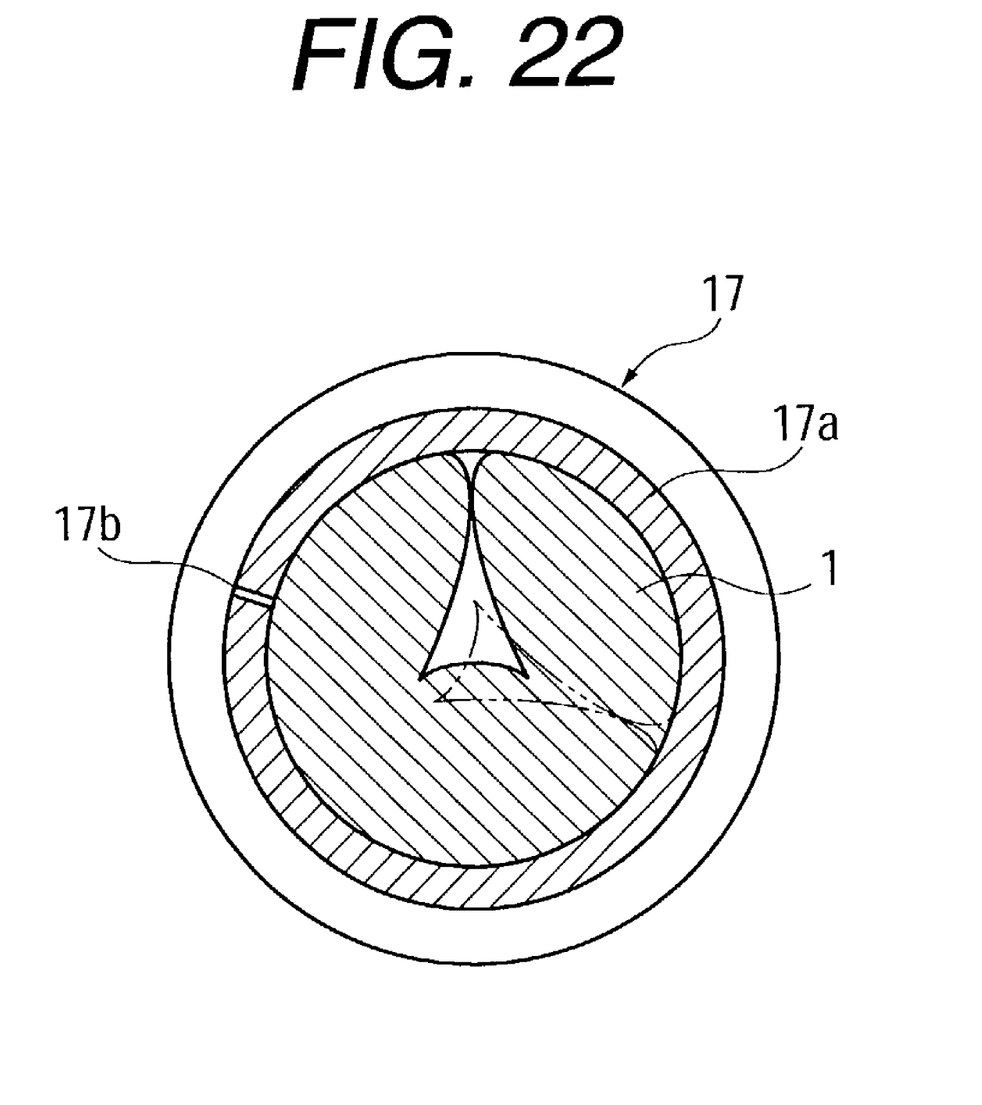
FIG. 22 is a cross sectional view showing operation of the insertion device of FIG. 18.

FIG. 19 is an enlarged perspective view of the insertion tube used in the insertion device; FIG. 20 is an enlarged perspective view of an insertion end portion of the insertion tube; FIG. 21 is a cross sectional view taken along line 21—21 of FIG. 20; and FIG. 22 is an enlarged sectional view showing operation of the insertion end portion of the insertion tube used in the insertion device.

In FIG. 18, reference numeral 11 denotes a device body; 12 denotes a push rod; 13 denotes a male-thread shaft; and 14 denotes a push-out mechanism.

Reference numeral 18 denotes an enclosing member. As shown in an enlarged manner in FIG. 19, the enclosing member 18 is provided with a lens receiving section 16 having a hinge portion 15; and an insertion tube 17 projects from the front end of the lens receiving section 16. A tip end portion 17a of the insertion tube 17 has an axially extending slit 17b. The lens receiving section 16 is constituted by a stationary half sleeve 19 and a movable half sleeve 20 whose lower edge portions are connected together by means of the hinge portion 15. Stationary and movable press plates 21 and 22 project from the stationary and movable half sleeves 19 and 20, respectively.

The conventional insertion device having the above-described structure is used as follows. The intraocular lens 1 is placed on the lens receiving section 16 of the enclosing member 18 and is folded into a smaller size before being loaded onto the insertion device body.

Upon completion of loading of the intraocular lens 1, the male-thread shaft 13 of the intraocular-lens insertion device is rotated in order to screw-feed the push rod 12. As a result, a process of inserting the intraocular lens into the eye starts.

The intraocular lens 1 is pushed forward gradually by the tip end of the push rode 12. When the intraocular lens 1 reaches the insertion end portion 17a of the insertion tube 17, the axially extending slit 17b of the insertion end portion 17a opens gradually. As a result, stresses in the optical portion 2 of the intraocular lens 1, which was completely folded at a base end side 17c of the insertion tube 17, are released gradually at the insertion end portion 17a. Subsequently, the intraocular lens 1 is inserted into the eye from an open end 17d.

During such insertion operation, the slit 17b holds the optical portion 2 of the intraocular lens 1 while sandwiching it, to thereby prevent abrupt discharge of the intraocular lens 1 into the eye. In addition, although the slit 17b releases stresses from the intraocular lens 1, the intraocular lens 1 is retained at the insertion end portion 17a, because cut surfaces located above and below the slit 17b hold the intraocular lens 1 from both sides thereof. Moreover, the slit 17b can control insertion speed of the intraocular lens 1 to match advancement speed of the push rod 12.

<Problems to be Solved by a First Aspect of the Invention>

However, since the insertion tube of the insertion device has no means for restricting rotation of the intraocular lens about the center axis of the insertion tube when the intraocular lens is pushed axially after being folded, as shown by an imaginary line in FIG. 22, the intraocular lens 1 may rotate in the circumferential direction of the inner wall surface of the insertion tube 17.

As a result, the positional relation between the slit provided at the tip end of the insertion tube and the folded intraocular lens changes, thereby making it impossible for an operator to eject the intraocular lens from the tip end of the insertion tube in desired conditions. Therefore, insertion direction and insertion speed of the intraocular lens are difficult to control with stability and high reproducibility, and therefore, operation of implanting an intraocular lens requires a high level of skill.

<Problems to be Solved by a Second Aspect of the Invention>

Moreover, the above-described conventional insertion devices have the following drawbacks.

The entire portion of the insertion tube, from the based end portion to the tip end portion, is formed of the same material, which is sufficiently strong to prevent the insertion tube from being broken by a lens moved through the insertion tube. Therefore, in the case in which the frictional resistance between the lens and the insertion tube is small, stress generated during deformation are released at a time when the lens is ejected from the tip end of the insertion tube into the eye, so that the lens flies out into the eye, possibly damaging the tissue within the eye.

In order to solve such a problem, insertion devices having a stress release structure have been proposed. One example of such a stress release structure is a slit which is formed to extend from the tip end of the insertion tube toward the base end portion thereof in order to gradually release stresses of a lens, and through which the lens is inserted into the eye.

Another example of such a stress release structure is a slant cut portion which is formed by obliquely cutting the insertion tube from the tip end of the insertion tube toward the base end portion thereof. The slant cut portion can release stresses gradually to thereby prevent flying out of a lens into the eye, which would otherwise occur upon sudden release of stress.

However, when a long slit extending from the vicinity of the base end to the tip end of the insertion tube is formed, or the angle of the slant cut portion is decreased in order to increase the length of the cut portion, to thereby release stresses more gently and thus enhance safety, the slit or cut portion faces the intraocular tissues in the vicinity of an incision. In this case, when the lens is inserted into the eye, the lens may come into contact with the tissue and damage it.

SUMMARY OF THE INVENTION

One object of the present invention is to provide an insertion device for a deformable intraocular lens which can restrict rotation of an intraocular lens about a center axis of the insertion tube in order to stably maintain insertion direction and insertion speed of the intraocular lens.

Another object of the present invention is to provide an insertion device for a deformable intraocular lens which can frictionally limit advancement speed of an intraocular lens at the time of stress release in order to prevent damage of the lens and enable more reliable insertion of the lens into the eye.

According to the first aspect of the present invention, there is provided an insertion device for inserting a deformable intraocular lens into the eye, in which a guide for an intraocular lens is provided on the inner surface of the insertion tube in order to restrict rotation of an intraocular lens about a center axis of the insertion tube when the intraocular lens is passed through the insertion tube in a folded condition. Accordingly, stable insertion operation is enabled, and operation for implanting an intraocular lens can be performed by an operator who does not have a high degree of experience. Moreover, since the posture of the intraocular lens within the insertion tube is stable, the insertion speed of the intraocular lens can be controlled stably.

According to the second aspect of the present invention, there is provided an insertion device for inserting a deformable intraocular lens into the eye, in which the insertion tube has a stress release structure for releasing stresses of the lens produced during deformation of the lens, and a frictional-resistance increasing structure provided on an inner surface of the insertion tube and in the vicinity of the stress release structure. Therefore, the lens can be inserted into the eye at slower speed as compared with conventional intraocular-lens insertion devices having the stress release structure only. Thus, the intraocular lens can be inserted into the eye safely.

The frictional-resistance increasing structure may be a roughened surface which extends over the entirety or a portion of the inner surface of the insertion tube along the circumferential direction.

BRIEF DESCRIPTION OF THE DRAWINGS

Various other objects, features and many of the attendant advantages of the present invention will be readily appreciated as the same becomes better understood by reference to the following detailed description of the preferred embodiments when considered in connection with the accompanying drawings, in which.

DETAILED DESCRIPTION OF PREFERRED EMBODIMENTS

Embodiments of the present invention will be described with reference to the accompanying drawings.

First, an intraocular-lens insertion device according to a first embodiment of a first aspect of the present invention will be described.

Figure 1:
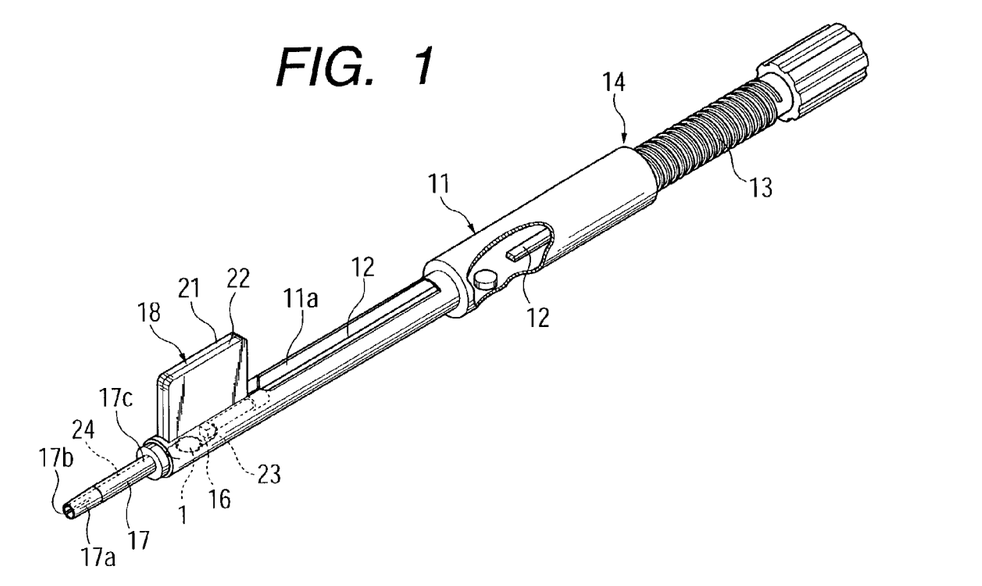
FIG. 1 is a perspective view of an intraocular-lens insertion device according to a first embodiment of a first aspect of the present invention.

FIG. 1 is a perspective view of the intraocular-lens insertion device according to the first embodiment of the first aspect of the present invention.

The intraocular-lens insertion device includes a generally cylindrical, tubular device body 11; a push rod 12 fitted into the device body 11; a push-out mechanism 14 including a male-thread shaft 13 in screw-engagement with a female thread (not shown) formed on the inner circumferential surface of the device body 11; and an enclosing member 18, which has a lens receiving section 16 having a hinge portion 15, and an insertion tube 17 projecting forward from the lens receiving section 16. An attachment groove 11a is formed in an upper portion of a tip end portion of the device body 11 to extend along the axial direction. The enclosing member 18 is loaded into the device body 11 via the groove 11a. The push rod 12 is rotatably connected to the male-thread shaft 13 and is supported by the device body 11 in such a manner that its rotation with respect to the device body 11 is restricted.

Figure 2:
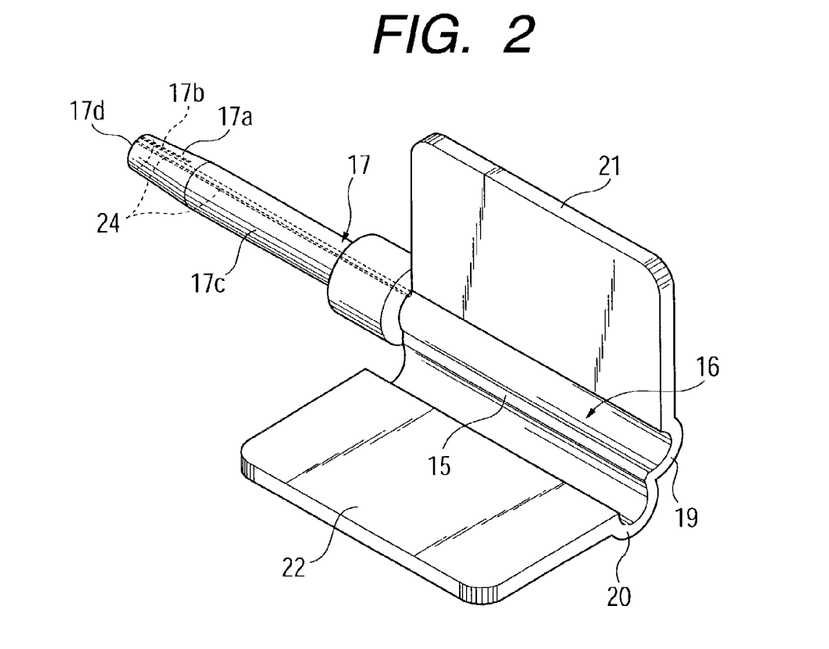
FIG. 2 is an enlarged perspective view of the enclosing member of FIG. 1.

FIG. 2 is an enlarged perspective view of the enclosing member, which is loaded into the tip end portion of the device body 11. As shown in FIG. 2, the lens receiving section 16 of the enclosing member 18 has a stationary half sleeve 19 and a movable half sleeve 20, whose lower edge portions are connected together by means of the hinge portion 15. The stationary half sleeve 19 is fixedly provided at the rear end of the insertion tube 17. The movable half sleeve 20 is located close to the rear end of the insertion tube 17 and can be opened and closed with respect to the stationary half sleeve 19. Stationary and movable press plates 21 and 22 project from the stationary and movable half sleeves 19 and 20, respectively.

The movable half sleeve 20, the hinge portion 15, and the movable press plate 22 constitute an open/close mechanism. When the open/close mechanism is closed, the movable press plate 22 comes into contact with the stationary press plate 21, so that the stationary half sleeve 19 and the movable half sleeve 20 form a tube that is coaxial with the insertion tube 17. When the movable press plate 22 is closed after placement of an intraocular lens 1 on the lens receiving section 16, the intraocular lens 1 is folded and deformed into a small size.

A base end portion 17c of the insertion tube 17 has an inner diameter equal to that of a tube which is formed by the stationary half sleeve 19 and the movable half sleeve 20 upon mutual contact. The insertion tube 17 has a tapered insertion end portion 17a at the tip end thereof. The insertion end portion 17a has an axially extending slit 17b.

The structure described above is substantially identical with that disclosed in Japanese Patent Application Laid-Open (kokai) No. 08-038542 (prior art).

Figure 3:
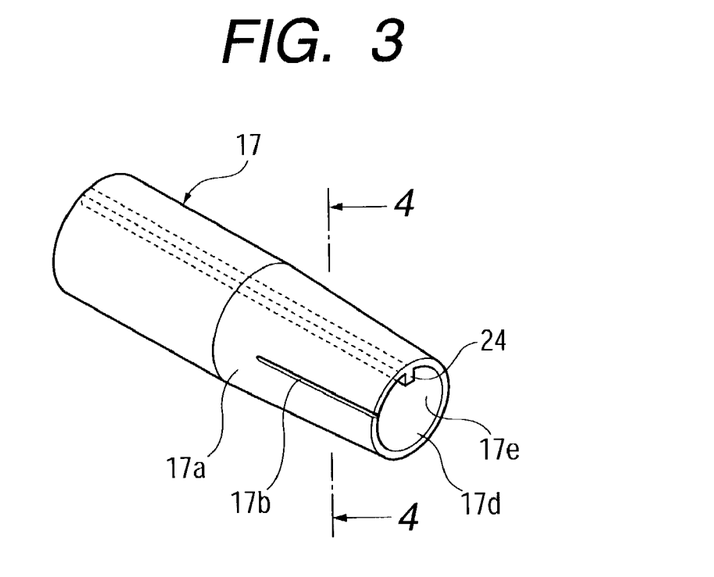
FIG. 3 is an enlarged perspective view of the insertion end portion of FIG. 1.
Figure 4:
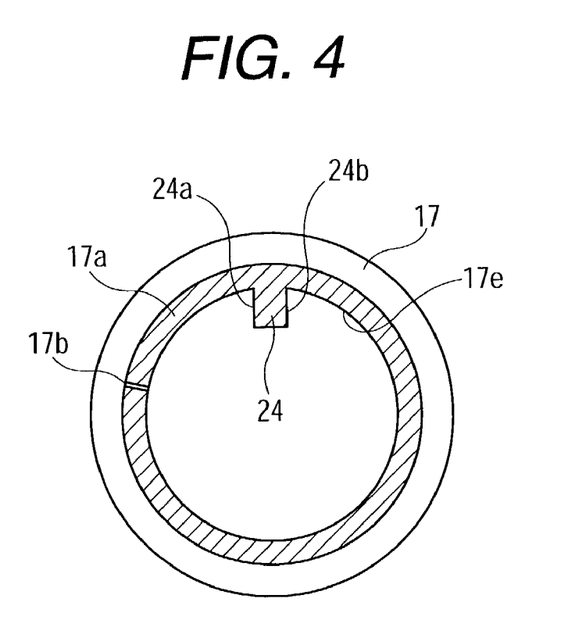
FIG. 4 is a cross sectional view taken along line 4—4 of FIG. 3.
Figure 5:
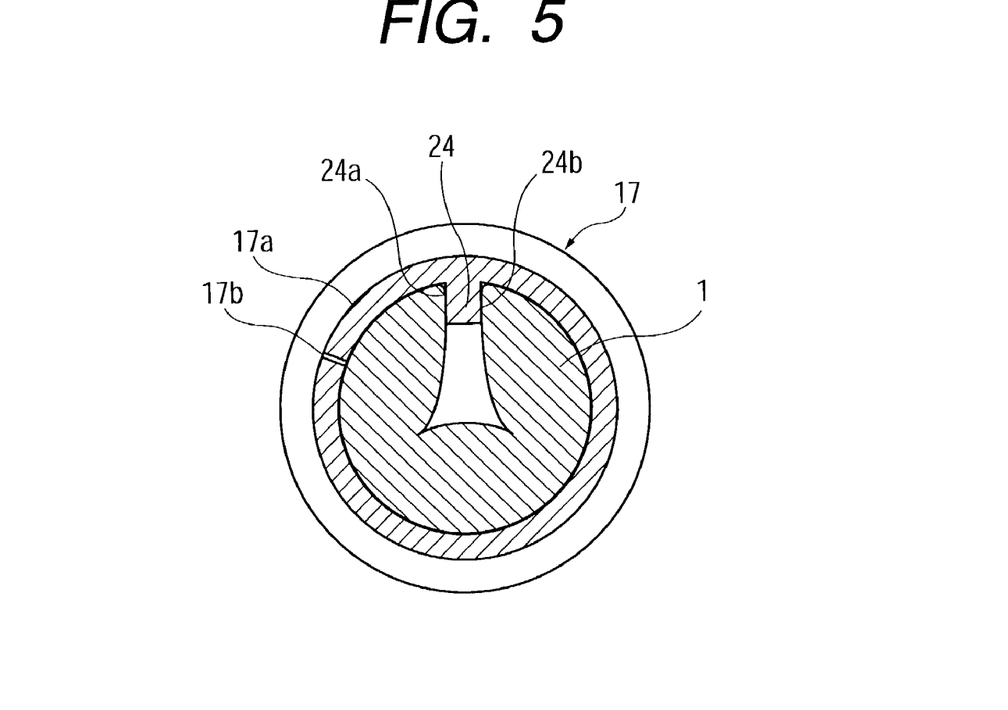
FIG. 5 is a sectional view of the device of FIG. 1, which is used for describing operation.
Figure 6:
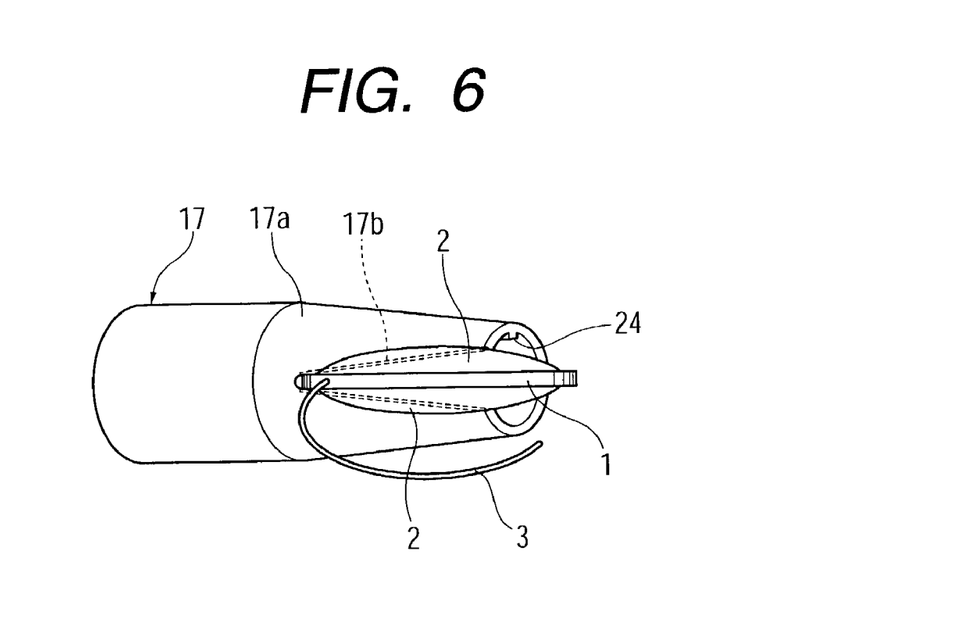
FIG. 6 is an enlarged perspective view of the insertion end portion of FIG. 1, which is used for describing operation.

FIG. 3 is an enlarged perspective view of the insertion end portion, which is formed at the tip end of the enclosing member of FIG. 2; FIG. 4 is a cross sectional view taken along line 4—4 of FIG. 3; FIG. 5 is an operation explanatory view showing a deformed intraocular lens located within the insertion tube of FIG. 3; and FIG. 6 is an operation explanatory view showing the intraocular lens as it is being ejected from the insertion end portion.

As shown in FIGS. 3 to 5, the intraocular-lens insertion device according to the first embodiment has a rail-shaped guide portion (projection) 24, which is formed on an upper portion of the inner wall surface 17e to extend parallel to the center axis of the insertion tube 17; i.e., to extend parallel to a direction along which the intraocular lens is pushed out. The, guide portion 24 restricts rotation of the folded intraocular lens 1 about the center axis, which rotation would otherwise occur when the intraocular lens 1 is pushed and moved. The guide portion 24 has a rectangular cross section and is formed integrally with the insertion tube 17. The guide portion 24 extends continuously along the axis of the insertion tube 17 from the base end portion 17c to the tip end portion 17a.

AS shown in FIG. 16, the intraocular lens 1 has a circular optical portion 2 and two symmetrically disposed supports 3. The circular optical portion 2 is made of an elastic material having predetermined memory characteristics. The supports 3 are made of a material different from that of the optical portion 2.

The intraocular-lens insertion device according to the first embodiment having the above-described structure is used as follows. First, the enclosing member 18 is removed from the attachment groove 11a of the device body 11. Subsequently, the movable press plate 22 and the movable half sleeve 20 of the enclosing member 18 are opened; and the optical portion 2 of the intraocular lens 1 is placed on the hinge portion 15 of the lens receiving section 16 while a predetermined clearance is formed therebetween, such that one support 3 of the intraocular lens 1 is located on the front side and the other support 3 of the intraocular lens 1 is located on the rear side. Subsequently, the movable press plate 22 and the movable half sleeve 20 are closed and brought into contact with the stationary press plate 21 and the stationary half sleeve 19, respectively, whereby the optical portion 2 is folded in half within the half sleeves 19 and 20 to thereby be deformed into a smaller size. Subsequently, the enclosing member 18 is attached to the attachment groove 11a of the device body 11.

After the insertion end portion 17a of the insertion tube 17 is inserted into an incision formed in the eye, the male-thread shaft 13 of the push-out mechanism 14 is rotated. As a result, the tip end portion 23 of the push rod 12 pushes the optical portion 2 of the intraocular lens 1 into the insertion end portion 17a of the insertion tube 17, whereby the optical portion 2 is gradually ejected into the eye while opening the slit 17b of the insertion end portion 17a.

When the intraocular lens 1 has arrived at the insertion end portion 17a, as shown in FIG. 5, opposite end portions of the folded intraocular lens 1 come into contact with opposite side surfaces 24a and 24b of the guide portion 24 formed on the inner wall surface 17e of the insertion tube 17. As a result, the intraocular lens 1 is pushed out by means of the tip end portion 23 of the push rod 12 while its rotation about the center axis of the insertion tube 17 is restricted.

Notably, the tip end portion 23 of the push rod 12 has a recessed portion which prevents interference with the guide portion 24 projecting inward from the insertion tube 17.

When the intraocular lens 1, which is pushed through the insertion tube 17 while being prevented from rotating about the center axis, arrives at the slit 17b formed in the insertion end portion 17a, one peripheral end portion of the intraocular lens 1 having engaged with the side surface 24a of the guide portion 24 projects from the slit 17b by virtue of elastic restoration force. Subsequently, the intraocular lens 1 is ejected from the slit 17*b* and an opening end 17*d* of the insertion end portion 17*a* while being allowed to restore its original shape.

According, the intraocular lens 1 can be restored to a shape close to its original shape at the time the intraocular lens 1 is nipped within the slit 17*b*, whereby the insertion direction and insertion speed of the intraocular lens can be controlled stably.

Figure 7:
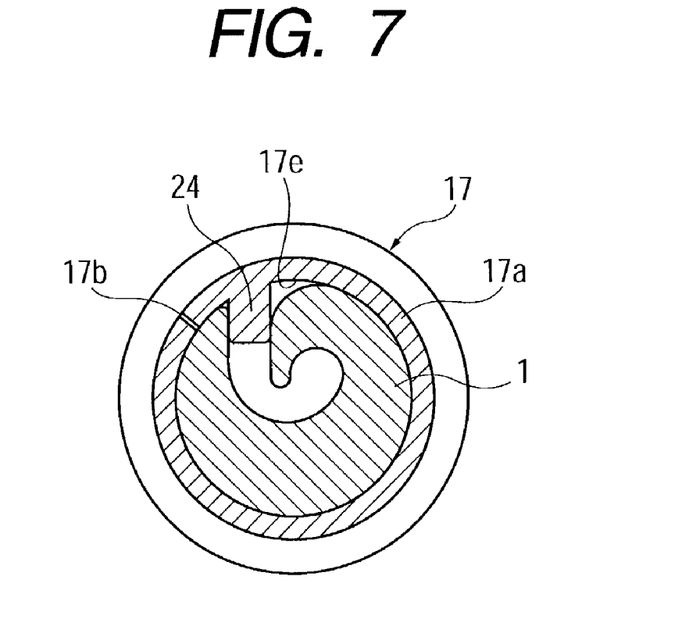
FIG. 7 shows a second embodiment of the first aspect of the invention.
Figure 8:
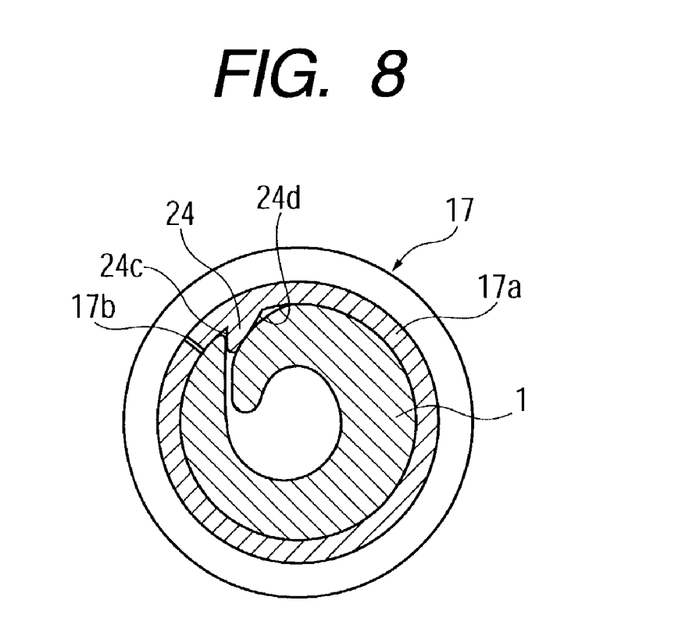
FIG. 8 shows a third embodiment of the first aspect of the invention.
Figure 9:
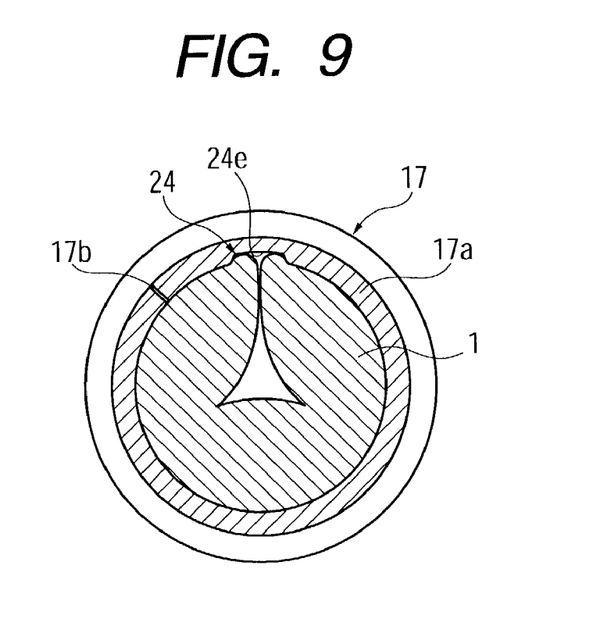
FIG. 9 shows a fourth embodiment of the first aspect of the invention.

FIGS. 7, 8, and 9 show second, third, and fourth embodiments, respectively, of the guide portion 24 according to the first aspect of the present invention.

In the embodiment of FIG. 7, the guide portion 24 is formed at a circumferential position shifted from the top portion of the inner wall surface 17*e* of the insertion tube 17 toward the slit 17*b*. That is, the guide portion 24 is located at a circumferential position offset from an intersection between the inner wall surface 17*e* and a plane passing through the center axis of the insertion tube 17 and extends substantially parallel to the plane.

In the present embodiment, as shown in FIG. 7, although one end of the intraocular lens 1 comes into contact with one side surface of the guide portion 24, the other end of the intraocular lens 1 is rounded inward by the other side surface of the guide portion 24. Thus, radial compression of the intraocular lens 1 is released, so that the intraocular lens 1 can be deformed without imparting excessive compression force to the intraocular lens 1.

In the embodiment of FIG. 8, the guide portion 24 is formed at a circumferential position shifted from the top portion of the inner wall surface 17*e* of the insertion tube 17 toward the slit 17*b*. Moreover, the guide portion 24 has a triangular cross section such that side surfaces 24*c* and 24*d* of the guide portion 24 each extending along the lens push-out direction form acute and obtuse angles, respectively, with respect to the inner wall surface. That is, the guide portion 24 is located at a circumferential position offset from an intersection between the inner wall surface 17*e* and a plane passing through the center axis of the insertion tube 17 and extends obliquely with respect to the plane. The guide portion 24 has a triangular cross section which is not axially symmetrical. The insertion device of the present embodiment is designed to roll rather than fold the intraocular lens 1.

The guide portion 24 of FIG. 8 has an asymmetric triangular cross section, and is disposed at a circumferential position offset from an intersection between the inner wall surface 17*e* and a plane passing through the center axis of the insertion tube 17. One side surface 24*c* of the guide portion 24 comes into contact with one end of the intraocular lens 1 to thereby restrict rotation about the center axis. The other side surface 24*d* of the guide portion 24 has a slant angle suitable to smoothly roll the intraocular lens 1. Thus, radial compression of the intraocular lens 1 is released, so that the intraocular lens 1 can be deformed more smoothly. Therefore, the insertion device of the present embodiment is effective for intraocular lenses having large diameters.

In the embodiment of FIG. 9, the guide portion 24 is constituted by a groove 24*e*, which is formed on the top portion of the inner wall surface 17*e* to extend along the axial direction. Due to the restoration force of the intraocular lens 1, the opposite ends of the intraocular lens 1 enter and move along the groove 24*e* formed on the inside surface of the insertion tube 17. Thus, rotation of the intraocular lens 1 about the center axis of the insertion tube can be prevented. The insertion device of the present embodiment is particularly effective for thick intraocular lenses.

In the above-described embodiments, intraocular-lens insertion devices which have the slit 17*b* formed in the insertion end portion 17*a* of the insertion tube 17 have been described. However, the present invention is not limited to these embodiments, and can be applied to insertion tubes, such as those disclosed in the above-described Japanese Patent Application Laid-Open (kokai) Nos. 5-103803 and 7-23990, which have ordinary insertion end portions not provided with a slit or cutaway.

Further, in the above-described embodiments, the guide portion 24 is formed integrally with the inner wall surface 17*e* of the insertion tube 17. However, the present invention is not limited to these embodiments, and can be applied to cases in which an elongated guide portion is formed separately and is welded or bonded to the inner wall surface 17*e* of the insertion tube 17.

Moreover, in the above-described embodiments, the guide portion 24 formed on the inner wall surface 17*e* of the insertion tube 17 assumes the shape of a single elongated straight projection. However, the guide portion 24 may be composed of a plurality of (e.g., two) rail-shaped projections which are formed to extend along the axial direction.

Next, an embodiment of the second aspect of the present invention will be described.

Figure 10:
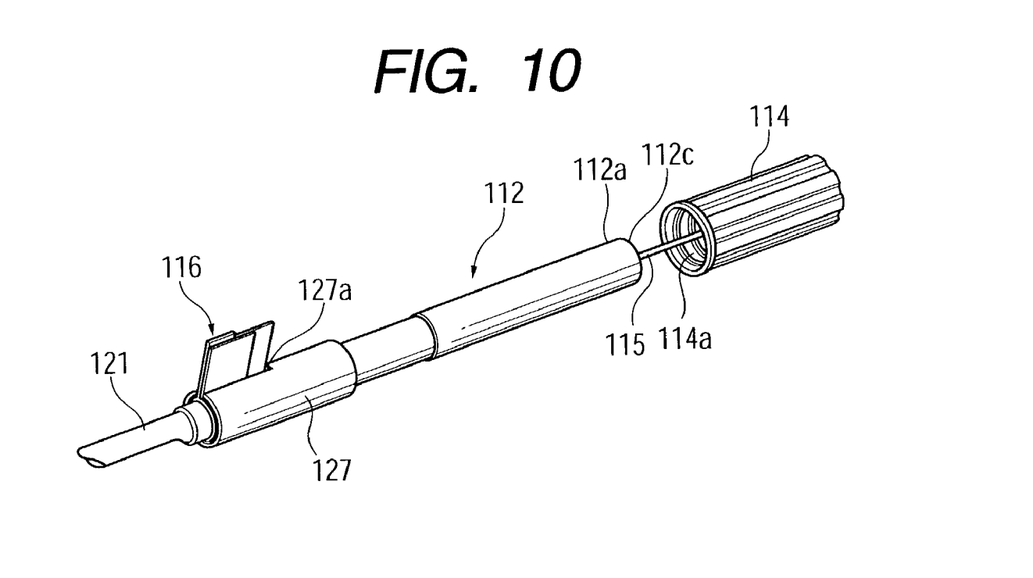
FIG. 10 is a perspective view of an intraocular-lens insertion device according to an embodiment of a second aspect of the present invention.

FIG. 10 is a perspective view of an intraocular-lens insertion device according to the embodiment of the second aspect of the present invention. The insertion device of the present embodiment includes a device body 112 which is identical with that disclosed in Japanese Patent Application Laid-Open (kokai) No. 7-23991, except for an insertion tube 121. A male thread 112*c* is formed on the outer surface of a rear end portion 112*a* of the device body 112. The male thread 112*c* is in screw engagement with a female thread 114*a* formed on the inner surface of an operation sleeve 114, which is provided in a push-out mechanism section.

The push-out mechanism section includes a push rod 115, which is disposed coaxially with the operation sleeve 114 and whose rear end portion is rotatably connected to the operation sleeve 114. An unillustrated rotation prevention mechanism permits the push rod 115 to move along the longitudinal direction and prohibits the push rod 115 from rotating with respect to the device body 112. The unillustrated tip end portion of the push rod 115 has a well-known shape suitable for pushing out an intraocular lens. An enclosing member 116 having a known structure is fitted into a tip end portion of the device body 112. After an unillustrated intraocular lens 1 is placed on the opened enclosing member 116, the opened enclosing member 116 is closed in order to fold the intraocular lens and holds the lens in the folded state. A slide stopper 127 is fitted onto the device body 112 in such a manner that the cylindrical slide stopper 127 can move axially but cannot rotate about the axis. The slide stopper 127 maintains the enclosing member 116 in a closed state by means of a groove 127*a* formed therein. The device body 112, the operation sleeve 114, the push rod 115, the enclosing member 116, and the insertion tube 121 formed integrally with the enclosing member 116 are each formed of a synthetic resin.

An intraocular lens 1 as shown in FIG. 16 is inserted as follows by use of the above-described insertion device. The intraocular lens 1 is composed of a circular optical portion 2 and supports 3. The supports 3 are made of a material different from that of the optical portion 2. The intraocular lens 1 is fixed within the eye by means of spring forces of the supports 3. The folded intraocular lens 1 is inserted into the eye as follows. An operator inserts the insertion tube 121 into the eye from which the lens has been removed, and then rotates the operation sleeve 114 in order to advance the push rod 115. As a result, the intraocular lens 1 is pushed out from the tip end portion of the insertion tube 121 and inserted into the eye. When the intraocular lens 1 comes out from the insertion tube 121 after movement through the insertion tube 121 by means of the push rod 115, the intraocular lens 1 restores its original shape before having been folded, due to elastic restoration force of the optical potion 2.

Figure 11:
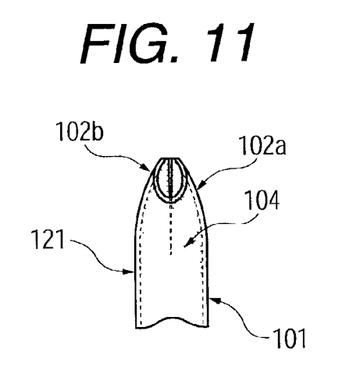
FIG. 11 is a left side view of the insertion tube of FIG. 10.
Figure 12:
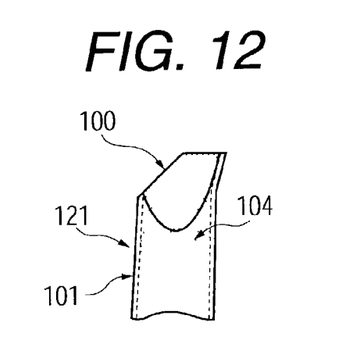
FIG. 12 is a plan view of the insertion tube of FIG. 10.
Figure 13:
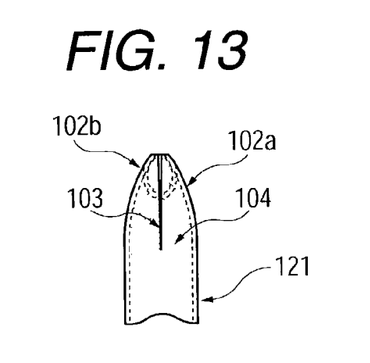
FIG. 13 is a right side view of the insertion tube of FIG. 10.
Figure 14:
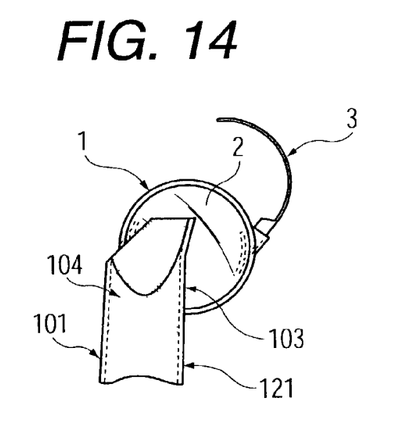
FIG. 14 is a plan view of the insertion tube showing the state of use thereof.

FIGS. 11, 12, and 13 shows a tip end portion of the insertion tube 121 according to the embodiment of the second aspect of the invention, wherein FIG. 11 is a left side view of the tip end potion, FIG. 12 is a plan view of the tip end potion, and FIG. 13 is a right side view of the tip end potion. As shown in FIG. 12, the tip end potion has a cutaway portion 100 for enabling the intraocular lens 1 to be inserted through a smaller incision, and a slit 103 serving as a stress release structure. As shown in FIG. 11, the tip end potion has flattened portions 102a and 102b for facilitating insertion of the tip end portion into an incision. FIG. 13 shows the flattened portions 102a and 102b and the slit 103, which extends from the tip end of the insertion tube 21 toward the base end portion thereof. As shown in FIG. 14, the tip end portion of the slit 103 is slightly curved to the right.

When the intraocular lens 1 has reached the base end portion of the slit 103 in the course of insertion of the intraocular lens 1, the slit 103 opens due to restoration force of the intraocular lens 1, and pushes a peripheral edge portion of the intraocular lens 1 to the outside of the insertion tube from the slit 103, while releasing stresses from the intraocular lens 1. If only small friction is produced between the intraocular lens 1 and the insertion tube 121 when the stresses of the intraocular lens 1 are released by means of the slit 103, the intraocular lens 1 restores its original shape at very high speed. In order to prevent this, a roughened portion 104 is provided to completely cover the inner surface in the circumferential direction of the insertion tube in the vicinity of the slit 103. The roughened portion 104 increases the frictional resistance between the intraocular lens 1 and the inner surface of the insertion tube 121 to thereby prevent high-speed restoration of the intraocular lens.

FIG. 14 shows a state in which the slit 103 has opened from the tip end portion of the insertion tube 121 due to restoration force of the folded intraocular lens 1, and a peripheral edge portion of the intraocular lens 1 has been pushed out from the slit 103 to the side of the insertion tube 121. After the peripheral edge portion of the intraocular lens 1 is pushed out from the slit 103, the stresses of the intraocular lens 1 are sufficiently but gently released by means of the roughened portion 104. Subsequently, the intraocular lens 1 is fixedly held in the slit 103 by means of restoration force thereof. When the push rod 115 is pushed further, the entire intraocular lens 1 is inserted into the eye.

Figure 15:
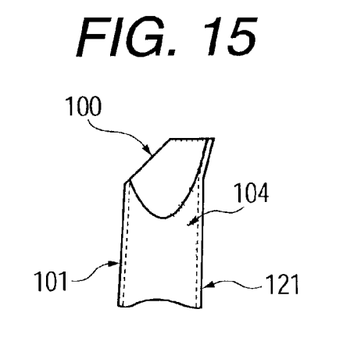
FIG. 15 is a plan view of the insertion tube showing another example of the structure for increasing frictional resistance.

FIG. 15 shows a structure in which a roughened surface is provided to cover a portion of the inner surface of the insertion tube. Even when the roughened surface is provided locally, insertion speed of the lens can be controlled as in the case shown in FIGS. 11 to 13.

In the present embodiment, flattened portions 102a and 102b are provided at the tip end portion of the insertion tube 121 in order to facilitate insertion of the tip end portion into an incision, and therefore, the interior volume of the tip end portion of the insertion tube 121 is small. Therefore, if the roughened portion 104 for increasing frictional resistance is not formed, when a center portion of a lens having the largest volume in a folded state passes through the vicinity of the root portion of the slit 103, its restoration force is released suddenly, and the intraocular lens 1 may be pushed out from the slit 103 at excessive speed. As a result, the supports 3 of the intraocular lens 1 as shown in FIG. 16 may damage the tissue of the eye.

In the present embodiment, frictional resistance between the insertion tube and a lens is increased by roughening the inner surface of the insertion tube in the vicinity of the slit 103, which serves as a stress release structure. However, the method of increasing the frictional resistance is not limited thereto. For example, the same effect can be obtained even when the roughened portion is formed through a process of coating a corresponding portion of the inner surface of the insertion tube with a material having a high degree of stickiness.

In the present embodiment, the stress release structure is in the form of a slit which is formed to extend from the tip end of the insertion tube to the base end thereof. However, the present invention is not limited thereto; the same effect can be obtained even when a slant cut portion is formed by obliquely cutting the insertion tube from the tip end toward the base end portion thereof, and a structure for increasing frictional resistance is provided on the inner surface of the insertion tube to be located in the vicinity of the slant cut portion.

Moreover, although the present embodiment uses an intraocular lens 1 shown in FIG. 16 whose optical portion 2 and supports 3 are formed of different materials, there can be used a lens as shown in FIG. 17A which has support portions 4 formed of the same material as that of the optical portion 2 and which is fixed within the eye by means of elastic force of the material itself.

Obviously, numerous modifications and variations of the present invention are possible in light of the above teachings. It is therefore to be understood that within the scope of the appended claims, the present invention may be practiced otherwise than as specifically described herein.

What is claimed is:

1. An intraocular-lens insertion device for deforming a deformable intraocular lens into a smaller size and inserting the intraocular lens into an eye, comprising:
    a device body;
    an insertion tube attached to a front end of the device body and adapted to be inserted into the eye;
    a push rod axially movable through the device body and the insertion tube and adapted to insert the intraocular lens into the eye when advanced;
    a push-out mechanism for advancing the push rod;
    a stress release structure provided on the insertion tube and adapted to release stress of the intraocular lens produced due to deformation thereof; and
    a frictional-resistance increasing structure provided on an inner surface of the insertion tube to be located in the vicinity of the stress release structure, the frictional-resistance increasing structure increasing frictional resistance between the inner surface of the insertion tube and the intraocular lens, said frictional-resistance increasing structure comprising a roughened surface which at least partially covers the inner surface of the insertion tube along the circumferential direction.

2. An intraocular-lens insertion device according to claim 1, wherein the stress release structure comprises one or a plurality of slits formed in the insertion tube to extend from a tip end toward a base end portion of the insertion tube.

3. An intraocular-lens insertion device according to claim 2, wherein the frictional-resistance increasing structure comprises a roughened surface which completely covers the inner surface of the insertion tube along the circumferential direction.

4. An intraocular-lens insertion device according to claim 1, wherein said roughened surface which completely covers the inner surface of the insertion tube along the circumferential direction.

5. An intraocular-lens insertion device according to claim 1, wherein said roughened surface which partially covers the inner surface of the insertion tube along the circumferential direction.

* * * * *